(12) United States Patent
Szczykutowicz et al.

(10) Patent No.: US 10,957,444 B2
(45) Date of Patent: Mar. 23, 2021

(54) APPARATUS FOR TOMOGRAPHY REPEAT RATE/REJECT RATE CAPTURE

(71) Applicant: Wisconsin Alumni Research Foundation, Madison, WI (US)

(72) Inventors: Timothy Peter Szczykutowicz, Madison, WI (US); Benjamin Thomas Viggiano, Madison, WI (US); Sean Douglas Rose, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 144 days.

(21) Appl. No.: 16/403,857

(22) Filed: May 6, 2019

(65) Prior Publication Data

US 2020/0357505 A1   Nov. 12, 2020

(51) Int. Cl.
*G16H 30/40*        (2018.01)
*G06T 7/00*         (2017.01)
*G16H 30/20*        (2018.01)

(52) U.S. Cl.
CPC .......... *G16H 30/40* (2018.01); *G06T 7/0012* (2013.01); *G16H 30/20* (2018.01); *G06T 2207/10081* (2013.01); *G06T 2207/10088* (2013.01); *G06T 2207/10104* (2013.01); *G06T 2207/10108* (2013.01)

(58) Field of Classification Search
CPC ...... G16H 30/20; G16H 30/40; G06T 7/0012; G06T 2207/10104; G06T 2207/10088; G06T 2207/10108; G06T 2207/10081
See application file for complete search history.

(56) References Cited

U.S. PATENT DOCUMENTS

| | | | |
|---|---|---|---|
| 6,754,675 B2 | 6/2004 | Abdel-Mottaleb et al. | |
| 9,317,580 B2 | 4/2016 | Cohen-Solal et al. | |
| 2010/0036248 A1 | 2/2010 | Chouno | |
| 2016/0128648 A1 | 5/2016 | Miyazawa | |
| 2018/0018773 A1* | 1/2018 | Canda | G06T 7/174 |
| 2018/0350081 A1* | 12/2018 | Hsieh | A61B 5/1121 |
| 2020/0043616 A1* | 2/2020 | Saalbach | G16H 30/40 |

FOREIGN PATENT DOCUMENTS

JP          2016186736 A       10/2016

OTHER PUBLICATIONS

International Search Report of International Application No. PCT/US2020/030069, dated Aug. 11, 2020.

\* cited by examiner

*Primary Examiner* — Brandon J Miller

(74) *Attorney, Agent, or Firm* — Boyle Fredrickson, S.C.

(57) ABSTRACT

A system for capturing possible repeats or rejections of images occurring during tomographic imaging accommodates the wide variety of imaging protocols by providing groupings of common imaging protocol types and highlighting outliers of this grouping. The grouping may consider text descriptions of the images and their series, machine parameters such as tomographic and localizer scans, and overlap between images of any given series.

20 Claims, 5 Drawing Sheets

APPARATUS FOR TOMOGRAPHY REPEAT RATE/REJECT RATE CAPTURE

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates generally to tomographic imaging equipment, including CT machines and the like, and in particular to a method and apparatus for measuring repeat rate/reject rate indicating tomographic acquisitions that are discarded or must be repeated.

Minimizing unnecessary medical imaging can help reduce the costs of healthcare and minimize the risk to the patient, for example, associated with radiation and contrast media exposure. An important class of unnecessary medical images are "reject" images resulting from patient motion, operator error, or in some cases machine error. "Reject" images require that the image procedure be repeated and for this reason are sometimes called. "repeat" images. These two terms will be used interchangeably herein.

The federal government requires a tracking of repeat images for mammography procedures (21 CFR § 900.12(e)(3)(ii)) and recommends it for standard x-ray radiography (21 CFR § 1000.55), Originally, tracking repeat images was simply a matter of comparing the number of photographic film sheets purchased versus the number discarded. Later, with the introduction of digital radiography and digital mammography (where there are no physical films) vendors offered a "at the scanner" method of tracking repeats. This method operates to send all scans to the physician unless the scan is marked by the technician as a "reject", where such a reject marking is automatically tallied by an automated repeat report. The technician is encouraged not to send "reject" images to the physician because the duplicate images will be immediately apparent to the physician (including the fact that one of them should have been rejected).

"At-the-scanner" solutions have not been offered for tomographic imaging machines. In part this is because "reject" images often, arguably, have some diagnostic value which justifies being sent to the physician. Further, the complexity of tomographic image sequences makes it difficult to immediately recognize that duplicate images have been obtained. This can be because the "repeat" image is an "add-on" image which simply extends the original scan coverage slightly and does not result in a new image "series", Recognizing duplicate images can also be complicated because physician orders for scanning a patient with different clinical motivations (for example a routine chest scan and a biphasic liver scan) may be combined and naturally produce images that appear to be overlapping or identical.

Even though it is difficult to track repeat rates in tomographic imaging, measuring and reducing repeat rates in tomographic imaging is arguably even more valuable than measuring repeat rates in radiography and mammography because of the high costs of tomographic imaging (which makes efficient use of the equipment and contrast media even more important) and because of the high radiation dose associated with some of these tomographic modalities.

SUMMARY OF THE INVENTION

The present invention provides an automated system for capturing repeats in tomographic imaging environments without requiring identification of rejects by the technician. A wide variety of different tomographic imaging protocols are evaluated by automatically generating an atlas of normal protocols through a grouping process. This grouping process establishes families of shared acquisition types so that infrequent protocols within these families having extra acquisitions can be identified as repeats with reasonable reliability, importantly, the system can work exclusively with the limited metadata associated with the acquired images and does not need modification of any current medical information system in use today.

Specifically then, in one embodiment, the invention provides an apparatus for capturing repeat rate/reject rate for tomographic modalities. The apparatus includes a data acquisition system receiving output data from tomographic scans. An electronic computer first extracts from output data information used to generate a signature for each study, the signature including tomography machine settings and text descriptions for each image and an overlap number indicating a number of acquisitions of the study having overlapping anatomical regions. Identical signatures are collected into groups and the groups joined into families based on similarities in the signatures of the groups, each family having a base group holding a largest number of signatures. Finally the computer outputs data identifying given signatures of each group based on a predetermined difference from signatures of the base group such as are likely to represent repeats or rejections.

It is thus a feature of at least one embodiment of the invention to provide a way of analyzing tomographic image studies by looking at the statistics of many studies rather than making a precise interpretation of physician orders.

The signatures of the base group are a subset of all other signatures in the family.

It is thus a feature of at least one embodiment of the invention to respect a superset/subset relationship between the signatures likely to reveal repeat scans.

The predetermined difference used to identify particular scans can be a predetermined number of extra scans in the given signatures compared to scans of the signatures of the base group.

It is thus a feature of at least one embodiment of the invention to highlight excess scans.

Alternatively or in addition, the predetermined difference may be a predetermined number of extra "localizer" scans (sometimes termed "scout" scans in CT) in the given signatures compared to the "localizer" scans of the signatures of the base group.

It is thus a feature of at least one embodiment of the invention to identify repeats in localizer scans which often do not have sufficient data to detect overlap.

Alternatively or in addition, the predetermined difference may be a predetermined value of the overlap number in the given signatures.

It is thus a feature of at least one embodiment of the invention to highlight scans that provide data of the same anatomical regions and thus are likely to be repeats.

The electronic computer may further evaluate the groups of each family and promotes at least one group outside of the base group to a new family based on the number of signatures in the group.

It is thus a feature of at least one embodiment of the invention to flexibly increase the number of groups (and hence base signatures) so that common image protocols are not erroneously identified as repeats. For example, an imaging center may commonly perform a head scan combined with a cervical spine exam on trauma patients. The presence of the "extra" cervical spine scan with the head scan may erroneously look like a repeat.

The electronic computer may extract image text descriptions and tomographic machine settings of images from each study and a group may be promoted if (1) at least one of the combinations of image text description and machine setting associated with the group are distinct from the combinations of image text description and machine setting associated with the base group and (2) the group has the most signatures of all groups belonging to the family except the base group.

It is thus a feature of at least one embodiment of the invention to create extra families in cases where the image text description and/or tomographic machine settings suggest that there are not repeats.

A group may be promoted only if a number of signatures in the group is greater than a predetermined percentage of the number of signatures in the base group, for example, 50 percent.

It is thus a feature of at least one embodiment of the invention to provide a system for generating families that can flexibly accommodate large and small base sets of tomographic data, for example, as may be found at different sized healthcare institutions.

The new family generated for a promoted group may also include groups whose signatures are supersets of at least one promoted group.

It is thus a feature of at least one embodiment of the invention to logically break the families into multiple families according to similarity with the original base group and the new promoted group.

The overlap number used in generating signatures may consider a number of images of the study having at least a predetermined percentage (for example, 50 percent) of overlap in anatomical spans.

It is thus a feature of at least one embodiment of the invention to avoid identifying as repeats images having de minimis overlap.

The generation of a signature may further identify "tack-on" images anatomically adjacent to an anatomical span of another image of the scan and having a length less than a predetermined percentage of the other image and wherein the predetermined difference is a number of tack-on images in the given signatures compared to the signatures of the base group.

It is thus a feature of at least one embodiment of the invention to identify tack-on images which are not repeats but which represent inefficient use of tomographic resources.

The apparatus may further include a white list having a set of words indicating studies that provide overlap and the electronic computer may further extract at least one of series text descriptions and study descriptions of images of each study and compare the them to the white list to output data identifying given signatures only if the at least one of the series text descriptions and study text descriptions associated with the given signatures do not match words of the white list. The white list may contain text descriptors well known in the art to convey the fact the study will contain more than one phase. For example, "with and without contrast" implies at least two image series are acquired corresponding to the absence and presence of imaging contrast.

It is thus a feature of at least one embodiment of the invention to eliminate from identification as repeats common repeated images having clinical purpose, for example, for contrast studies with delay phases or the like.

The output data may identify given signatures as a function of at least one of the group consisting of a technician obtaining a scan of the given signatures, a protocol of the scan of the given signatures, and a tomographic machine acquiring tomographic scans of the given signatures.

It is thus a feature of at least one embodiment of the invention to provide a versatile output report that can help identify opportunities for technician training, difficult procedures or machines, or equipment failures.

The step of extracting image signature data may review at least one of the DICOM headers of all images output from the set of machines and selected DICOM headers of selected images and/or a log file providing data for non-selected images;

it is thus a feature of at least one embodiment of the invention to provide a system that can work with standardized DICOM headers or log files without the need for direct access to the physician order and data.

The base groups may be identified from signatures selected by the technician for uploading to an image archive.

It is thus a feature of at least one embodiment of the invention to use technician self-selection to help identify repeats.

These particular objects and advantages may apply to only some embodiments failing within the claims and thus do not define the scope of the invention.

DETAILED DESCRIPTION OF THE PREFERRED EMBODIMENT

Figure 1:
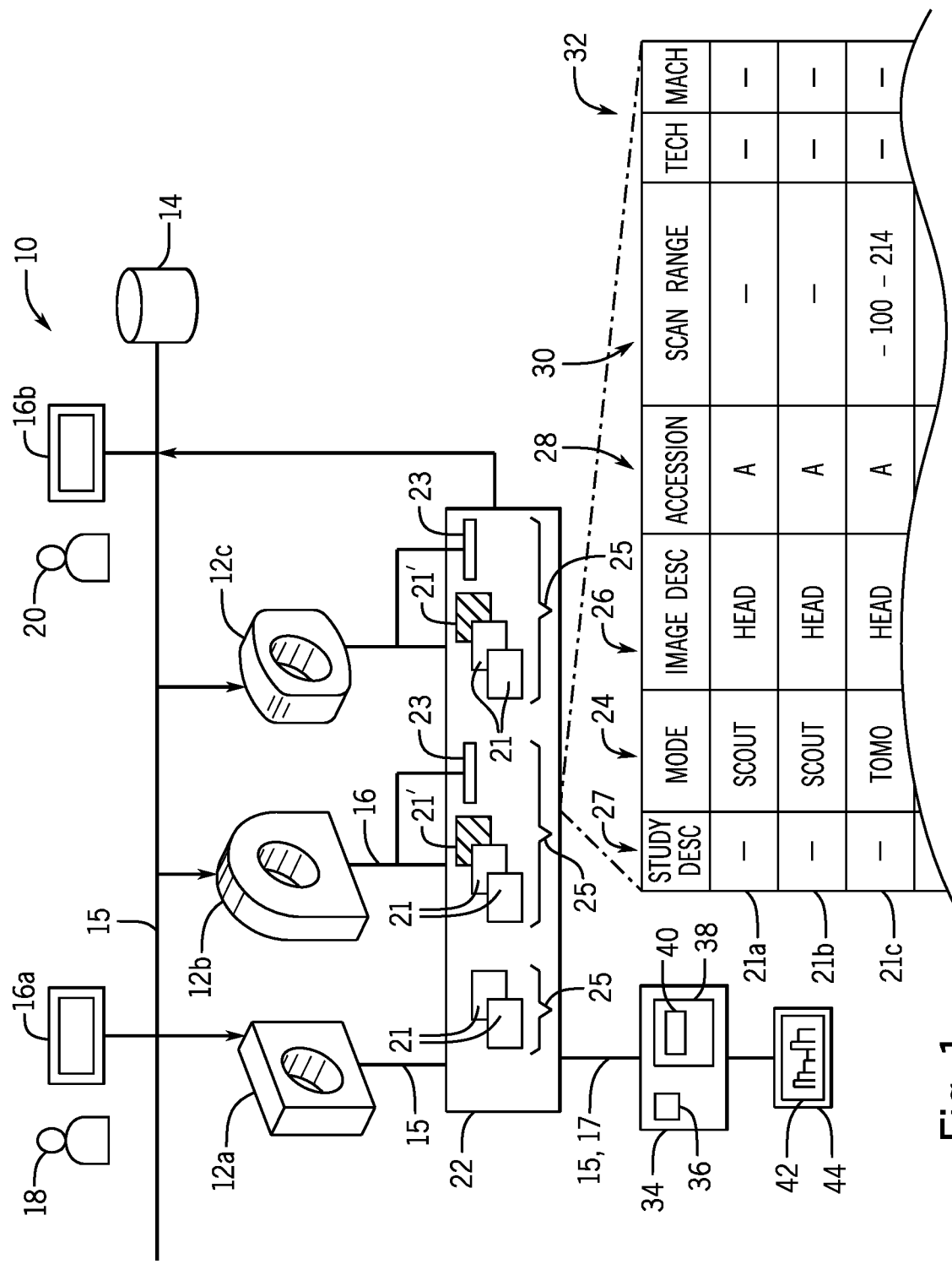
FIG. 1 is a block diagram of a tomographic imaging facility having multiple tomographic imaging machines communicating with an electronic medical record system and showing the collection of output data from the tomographic imaging machines using a dedicated computer having a display system.

Referring now to FIG. 1, a tomographic imaging facility 10, for example, a hospital or other healthcare facility, may provide for one or more tomographic imaging machines 12a-12c. These tomographic imaging machines 12 may include but are not limited to one or more computed tomography (CT), positron emission tomography (PET), single-photon emission computed tomography (SPECT), and magnetic resonance imaging (MRI) systems. As is understood in the art, such tomographic imaging machines 12 provide for tomographic or cross-sectional images developed using special reconstruction algorithms operating on a variety of different data types.

Generally each of the tomographic imaging machines 12 will produce images according to scan parameters describing the operation of the tomographic imaging machines 12 during a scanning to obtain an image. For example, a scan parameter may provide for a localizer scan in which a single planar projection (non-tomographic) image is taken along an inferior-superior axis of the patient. Such localizer scans are used both clinically and to provide reference points for tomographic scans. Alternatively the scan parameter may provide a tomographic slice where, for example, a helical scan is used to acquire data over multiple voxel's of a volume of the patient. Such volumetric data may be reconstructed into a set of tomographic slice images aligned with an arbitrary plane or as a three-dimensional model or other volumetric representation. As used herein, the term "image" will refer both to a single planar projection image or a set of tomographic images over a volume.

The tomographic imaging machines 12 may be connected via a network 15 with an electronic medical record (EMR) system 14 and with multiple terminals 16a and 16b being standard computer type terminals. Terminals 16 allow for communication with the EMR, the latter of which may be used to record or retrieve clinical data about patients and to conduct physician orders to other service providers including a radiologist or a pharmacy, or to the tomographic imaging machines 12 as operated by technicians (not shown). In a typical tomographic image workflow, a physician 18 may enter an imaging order for a type of tomographic scan using operating terminal 16a. The imaging order may provide for a text description of the desired set of images (a "study" description) as well as a particular type of tomographic imaging machine 12 and will identify a patient to be imaged. This imaging order may be sent directly to the technicians associated with the tomographic imaging machines 12 or to a terminal 16b of a radiologist 20 who reviews and forwards the order to a technician operating the particular tomographic imaging machines 12. Imaging orders may come directly from the radiologist 20 as well.

Upon completion of the imaging order by the technician as executed on tomographic imaging machines 12, image data and metadata about the image (henceforth collectively termed images 21) may be sent from the tomographic imaging machines 12 over the network 15 to the electronic medical record (EMR) system 14 and/or to a separate archive 22 accessible by the EMR system 14. Generally the archive 22 may include all images 21 produced by the tomographic imaging machines 12 including those rejected by the technician by appropriate setting of the tomographic imaging machines 12. Alternatively tomographic imaging machines 12 may be set to allow the technician to reject particular images 21' (shown diagrammatically in the archive 22 as shaded images). These rejected images 21' are not stored in the archive 22 but nevertheless may have their metadata captured by a log 23 which is stored in the archive 22.

Normally sets of images 21 will be connected to a study 25 having multiple images 21 and identified by a study number (called accession identifier). The images 21 in a study 25 will typically be of a single patient and will be taken contemporaneously in a single imaging session. Nevertheless, the images 21 in a study 25 will typically be varied covering different portions of the patient's anatomy and may include both localizer and tomographic scans. In some cases, the images 21 of a study 25 can relate to different clinical questions about the patient.

As noted, generally the images 21 will include both image data (pixels or voxels defining the image) and metadata describing the image characteristics typically in the form of a DICOM header of type well known in the art. For multiple images 21a-21c, this metadata may include data indicating a scanning mode 24 of the tomographic imaging machines 12 (for example, localizer mode or tomographic mode as discussed above). The metadata may further include "image" text descriptions 26 of the image 21 as well as "study" text descriptions 27 describing collectively all of the images of the study 25. For example, the image text description 26 may be "head" whereas of the study text description 27 might be "CT head without IV contrast." The study text description 27 will be the same for each study 25 but the image text description 26 may change. Generally, the image text descriptions 26 will be considered to be a text descriptions directed to an individual image whereas the study text descriptions 27 will be descriptions common to multiple images of the study.

The metadata for each image 21 will also include an accession identifier 28 (shown as a letter) uniquely identifying the study and a scan range 30 generally indicating an axial length along the patient's superior/inferior axis of a volumetric data acquisition and expressed, for example, in millimeters relative to a fixed landmark of the patient common among all of the images of the study. Not all scanning modes 24 will have scan ranges 30. The metadata may include additional data 32 indicating the technician acquiring the image and indicating the tomographic imaging machines 12 on which the image 21 is obtained.

The present invention may provide an independent computer server 34 or the like providing a connection 17 (for example, providing data acquisition circuitry such as a network interface for communicating with the archive 22 and/or network 15) so that the computer server 34 may access the data of the archive 22 including the images 21 and/or data logs 23. Generally computer server 34 will include one or more processors 36 communicating with electronic memory 38 having a program 40. As will be discussed in more detail below, this program 40 works in conjunction with the data acquisition circuitry to process the data of the archive 22 and provide output reports 42 on an associated electronic display 44. While an independent computer server 34 is described, the invention contemplates that the program 40 may be distributed among multiple or other single locations including, for example, a server implementing the archive 22 or electronic medical record system 14.

Figure 2:
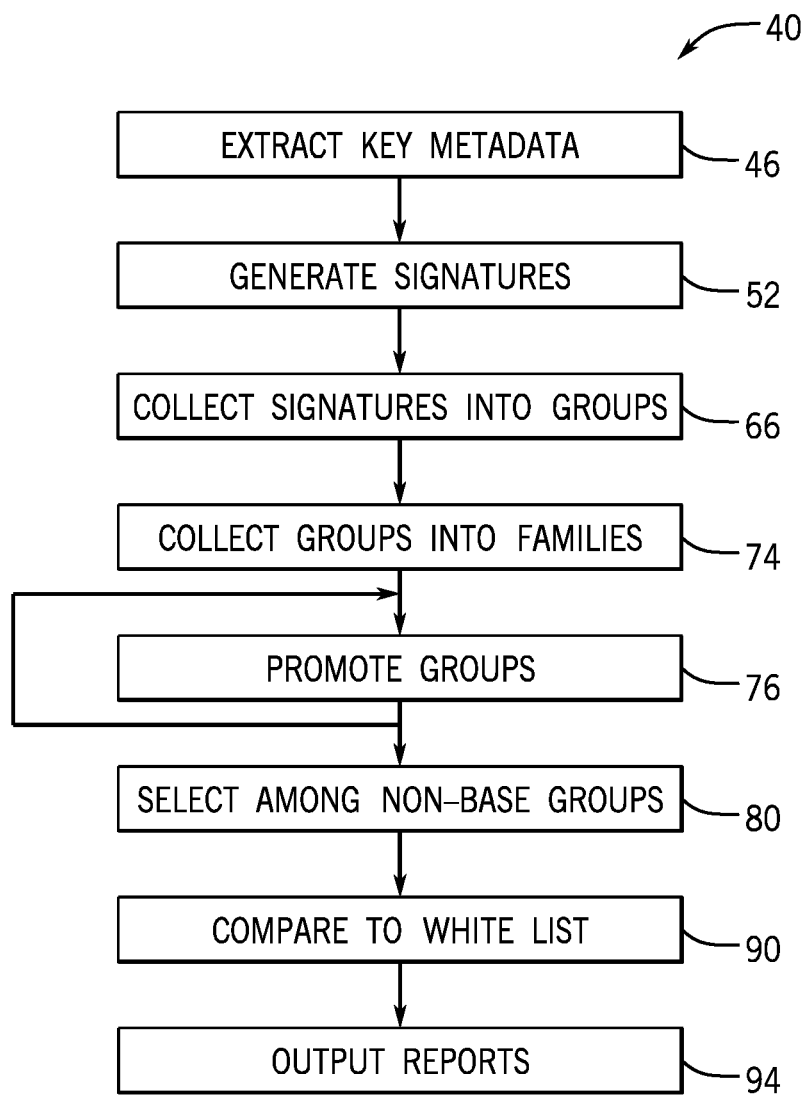
FIG. 2 is a flowchart of a program executed by the computer of FIG. 1 for the purpose of identifying anomalous scans associated with repeats/rejects.

Referring now to FIGS. 1 and 2, at a first step of the program 40 indicated by process block 46, data from the archive 22, for example, including all scans performed during a given interval (and desirably being hundreds or thousands of images 21), may be read by the computer server 34. This data desirably includes metadata of all images taken during that interval including images 21 and rejected images 21' either from the headers of the images 21 or a combination of the headers of the images 21 and information from the logs 23. At this process block 46 metadata from only images 21 and not images 21' may also be identified for use in building base groups as will be discussed below in one embodiment.

Figure 3:
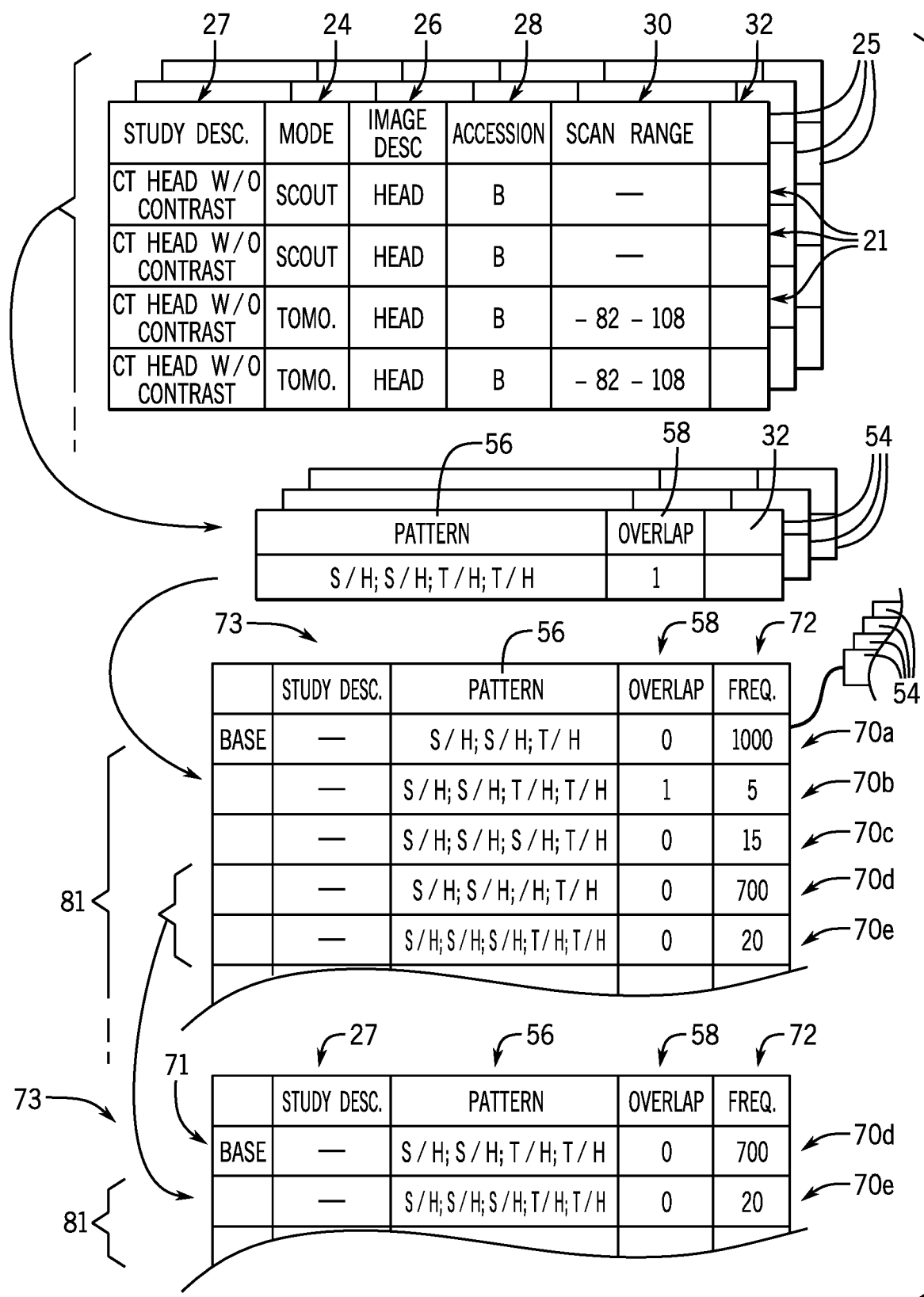
FIG. 3 is a data diagram showing the processing of the output data of FIG. 1 by the computer of FIG. 1 during the steps of the program of FIG. 2.

Referring now to FIGS. 1-3, this extraction process of process block 46 will produce a set of studies 25 each providing the metadata shown in FIG. 1 for a single study number (having identical accession identifiers 28). In this example, a first image 21 of a study 25 may provide for a study text description 27 of "CT head without contrast," a mode 24 of "localizer," an image text description of "head," and an accession identifier of "B" and no scan range. Additional data 32 of technician and machine are not shown for clarity but will typically be identified and identical for each image 21.

The second image 21 may be similar to the first image 21 and may represent a second localizer scan (for example, lateral versus anterior/posterior). The third and fourth records may also be similar and provide for a tomographic mode 24 and image text description 26 of "head" and accession identifier 28 of "B" and a scan range 30 of –82-108. The study text description 27 and additional data 32 may be the same as the previous images 21. Although only a few studies 25 are shown, generally there will be many hundreds or thousands of such studies 25 collected during the process block 46.

Referring particularly to FIGS. 2 and 3, at process block 52, each of the studies 25 is compressed to a signature 54. The signature 54 will generally include the common study text description 27 of each image 21 discussed above and a signature pattern 56 formed by pairs of scanning modes 24 and associated image text descriptions 26 for each image 21 together concatenated as a string. In the depiction. FIG. 3, the scanning mode 24 and image text description 26 of "localizer" and "head" have been simplified as and the image text descriptions 26 of "tomographic" and "head" have been simplified to "T/H" so that the signature pattern 56 provides the concatenated elements of "L/H; L/H; T/H; T/H" The order of the elements within the signature pattern 56 is disregarded by the program 40.

The signature 54 may also include an overlap number 58 indicating the number of images 21 having overlapping scan ranges. This overlap may be determined by a comparison of the scan ranges 30 or alternatively a similarity analysis of each image 21 (or each slice within each image) with respect to other images 21. Each signature 54 is also associated with the additional data 32 indicating the technician and tomographic imaging machines 12 and the study number 27, although these are not part of the signature for grouping purposes as described below.

Figure 4:
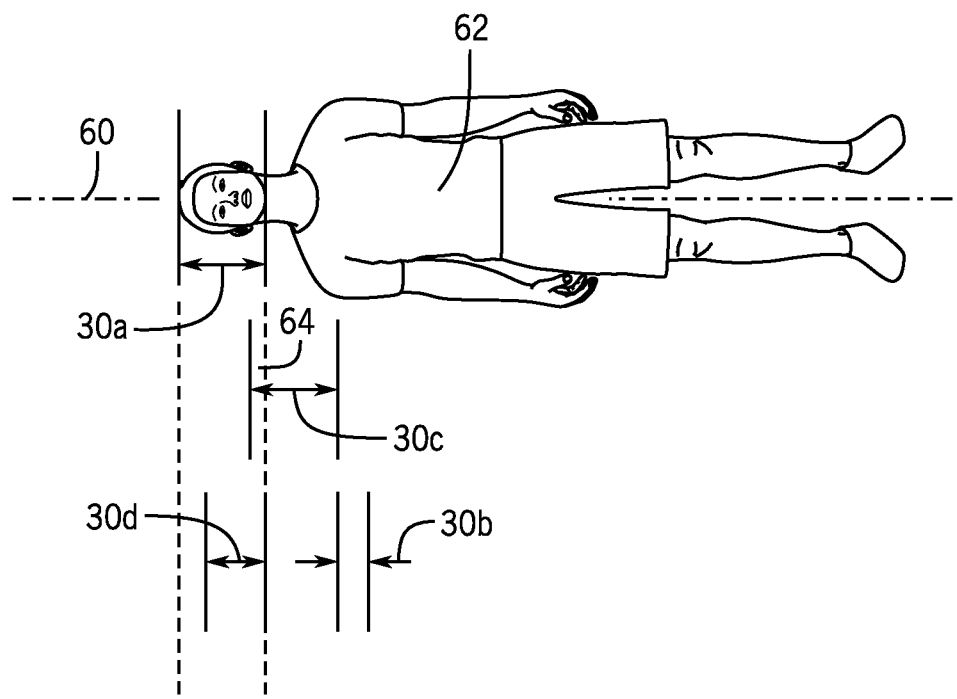
FIG. 4 is a simplified top plan view of a patient showing anatomical spans of different images relevant to the characterization of overlap and tack-on images of the present invention.

Referring momentarily to FIGS. 3 and 4, as noted, the values of the scan ranges 30 indicate positions along a superior/inferior axis 60 flanking a volume of the patient 62 being scanned. Different images 21 of a given accession identifier 28 may provide different scan ranges 30a-30d depicted diagrammatically where, for example, scan range 30a covers the entire head of the patient 62, scan range 30b begins within the scan range 30a within the patient's head and then proceeds in an inferior direction over the cervical spine and upper chest of the patient 62. The scan ranges 30a and 30b technically overlap but in one embodiment of the present invention, an overlap is counted only if the actual overlapping amount 64 is greater than 50% and preferably greater than 60% of the larger of the overlapping scan ranges 30a and 30b. Thus, scan range 30b would not be considered overlapping with scan range 30a based on the minor overlap. On the other hand scan range 30d, which starts within scan range 30a and concludes at the conclusion of scan range 30a, covers more than 60% of scan range 30a (or greater than 50%) and thus would be considered overlapping.

As will be discussed in more detail below, the analysis of overlap may also identify a tack-on range 30c which may be stored as part of the signature pattern 56. A tack-on range 30 such as tack-on 30c is not contained within any other scan range 30 and has a length along the superior/inferior axis 60 of less than 30 percent of the length of the longest scan range 30. Tack-on regions may be indicated in the signatures 54 as a separate part of the signature pattern 56 (not shown for clarity).

Referring again to FIGS. 1-3, in this way multiple signatures 54, one associated with each study 25, may be created. Each of the signatures 54 is linked with other data of the corresponding study 25 including, for example, accession identifiers 28 and additional data 32 so this information is not lost.

Referring again specifically to FIG. 2, at succeeding process block 66, identical signatures 54 are then collected in corresponding groups 70a-70e. Each of the groups 70 is tagged with a frequency number 72 indicating the number of signatures 54 within that group and thus the number of studies 25 represented by that group 70. The groups 70 identify the patterns 56 of the underlying signatures 54 and the overlap number 58 and may be linked to the constituent signatures 54, for example, by storing accession identifiers 28 so that a given group 70 may be associated with particular study descriptions 27, technicians, and tomographic imaging machines 12 (which need not be identical for the given group 70).

As indicated by process block 74, the groups 70 are then collected into families 73 according to similarities among the groups 70. This collection process may be performed by sorting and repeated promotion as will now be described. Per process block 74 all of the groups 70 may be sorted in the order of lowest overlap number 58, followed by shortest signature pattern 56, followed by largest frequency number 72.

After this sorting, the first group 70 of the sort is identified as a base group 71. This base group 71 by virtue of the sorting process will have the smallest overlap number 58 (no greater than the overlap number 58 of any other group 70) and shortest pattern 56. This signature pattern 56 of the base group 71 is then compared to each next group 70 to see if the signature pattern 56 of the next group 70 is a superset of the scan pattern of the base group 71. This determination of supersets is without regard to the order of the elements of the signature pattern 56.

If the next group 70 is a superset of the base group 71 then this next group 70 remains in the family 73 otherwise it is promoted to a new family 73 per process block 76 together with all groups 70 lower in the sorting order that are supersets of the promoted group 70. At the conclusion of this process, all groups 70 within a given family 73 will provide successively greater supersets of the base group 71.

At the conclusion of this process, as still indicated by process block 76, in a second promotion phase, each family 73 is then evaluated with respect to possible group promotions within that family based on the frequency number 72 associated with that group 70. In this promotion process, groups 70 that are not the base group 71 are reviewed to see whether their frequency number 72 is at least 65% of the frequency of the base group 7L If so, that group 70 (e.g., group 70d in the example of FIG. 3) is promoted to a new family 73'.

At the conclusion of this process, as still indicated by process block 76, in a third promotion phase, each family 73 is then evaluated with respect to possible group promotions within that family based on the frequency number 72 associated with that group 70 and the signature pattern 56 associated with that group. If a group 70 has the highest frequency number among all groups in the family 73 except the base group 70*a*, and its signature pattern 56 contains scan modes 24 and/or image text descriptions 26 that are distinct from those in the signature pattern of the base group 70*a*, then the group is promoted to a new family. Distinct in this context means that the combination of the scan mode 24 and image text description 26 is not found anywhere in the signature pattern 56 of the base group 70*a*. Thus for example, if the base group signature has only L/H and T/H combinations (discussed above) a T/C (tomographic/cervical spine) scan mode/image text description would be considered distinct. Following this process, each family 73 is reviewed to see if it contains more than one group 70. If not, that family is removed from consideration with respect to identifying repeats or rejects.

The invention also contemplates that the base groups 71 may be identified or confirmed by looking at non-rejected images 21 (exclusive of rejected images 21') under the assumption that these former images will only be non-reject sequences.

At process block 80, each of the families 73 is reviewed to identify potential repeat/reject groups 70 which in the broadest sense may be all non-base groups 81 that is, all groups 70 that are not base groups 71. More typically, selected of these non-base group 81 will be identified according to whether there is any overlap (overlap number greater than zero) and these identified groups are used in an output report. Other contemplated selection criteria include selecting any of the non-base groups 81 that has more than a predetermined number of elements (e.g., "L/H" or "T/H") in the pattern 56 than the base group 71 of its family 73. Another contemplated criterion is to select those of the non-base groups 81 that have more than a predetermined number of pattern elements that are localizer scans than the localizer scans found in the base group 71 of the particular family 73. As noted, the signature pattern 56 may include a designation as to whether there is a tack-on image, and this designation as a tack-on image may also be used to select among particular of the non-base groups 81 for studies 25 including repeats or rejections. The frequency of the non-base groups 81 may be used as a statistic value to identify the number of rejects/repeats of any particular group 70 that is identified.

Figure 5:
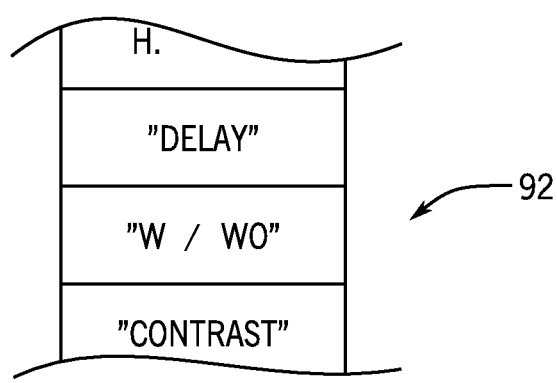
FIG. 5 is a simplified representation of a white list that may be used to further refine an understanding of repeat images.

Referring now to FIGS. 2 and 5, at process block 90, after selection of non-base groups 81, the selected signatures 54 from the non-base groups 81 may have their study text descriptions 27 and image text descriptions 26 compared against a white list 92 of words that are associated with situations in which, for example, designation as a repeat or rejection may not be warranted. The white list 92 may be stored in the memory 38 of the computer server 34 and may be developed empirically.

Situations intended to be detected by the white list 92 include studies 25 in which there is a delayed acquisition (two successive acquisitions of the same anatomy based on a change in physiological state) or where there is a contrast media injection and two images of the same anatomical region are obtained to provide a comparison between contrasted and non-contrasted tissue. The white list 92 may therefore include words or phrases associated with the situation such as "delay," "w/wo," and the like. A matching of words of the white list 92 to the study text descriptions 27 or image text description 26 removes the given signature 54 from consideration in the statistics collected with respect to repeat or rejection to reduce false identification of reject repeats.

Figure 6:
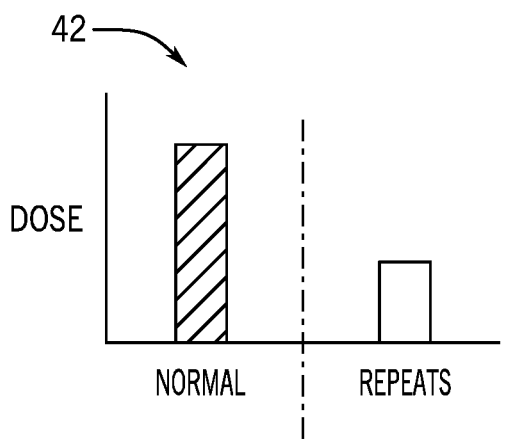
FIGS. 6-9 are example reports generated by the present invention on the display system of FIG. 1.

Referring now to FIG. 2 and in particular to FIGS. 6-9, the statistics of the non-base groups 81 after culling by the white list 92 per process block 90 may be displayed, for example, on the display 44 of FIG. 1 in the form of one or more charts. In FIG. 6, one chart may provide an estimate of the radiation dose associated with "normal scans" of each base group 71 and "repeat/rejection" scans of the identified non-base group 81, This radiation dose (for example, for CT) may be estimated using an empirically derived table that relates the scanning mode 24 and image text description 26 and scan range 30 to a particular radiation dose. This particular radiation dose may be multiplied by the frequency of each of these groups (71 and 81) to provide a quantitative comparison.

Figure 7:
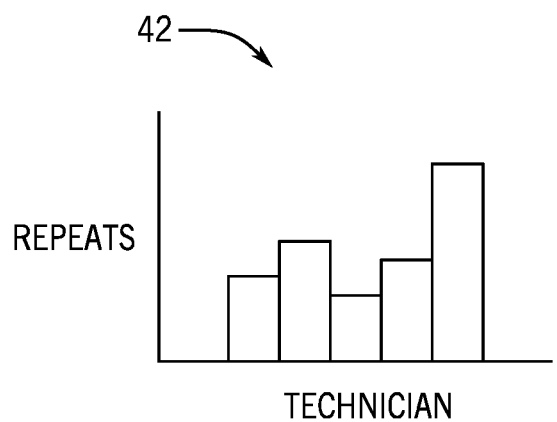

Similarly as shown in FIG. 7, the number of scans associated with repeats or rejections may be displayed by displaying a frequency of the identified non-base groups Si according to technician identifiers retained in the signatures 54 as discussed above. This display may help identify technicians who need additional training.

Figure 8:
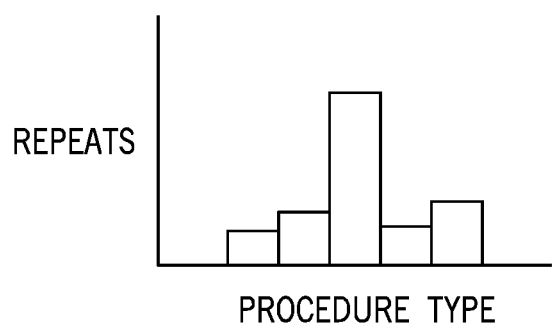

Alternatively, as shown in FIG. 8, the number of scans associated with repeats or rejections may be displayed as divided among procedure type extracted from the study text descriptions 27 mentioned above. Such a report may, for example, indicate that tomographic brain scans have more repeats than abdomen scans also pointing out a training opportunity.

Figure 9:
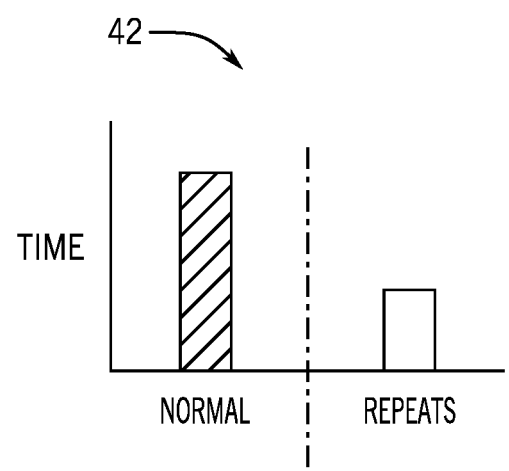

A similar display to that of FIG. 6 may be made as shown in FIG. 9 by providing a display indicating the excess time devoted to repeat/reject scans. These time estimates may again be prepared from an empirically derived table linking a particular table of empirically collected values indicating the time required for given scans to provide a comparison between the modes and image descriptions with estimates of the time required to complete the scans associated with those modes and imaging descriptions.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. An apparatus for capturing repeat rate/reject rate for tomographic modalities comprising:
   a data acquisition system receiving output data from tomographic scans, the output data related to images collected into studies having study numbers and associated with a particular patient and contemporaneous images; and
   an electronic computer executing a program stored in non-transitory medium to:
   (a) extract from output data of each image of each study a tomography machine setting for each image and a text description of each image;
   (b) generate a signature from the extracted data of each study having a study number, the signature including tomography machine settings and text descriptions for each image and an overlap number indicating a number of images of the study having overlapping anatomical spans;
   (c) group identical signatures into groups and collect the groups into families based on similarities in the signatures of the groups, each family having a base group holding a largest number of signatures; and
   (d) output data identifying given signatures of each group having a predetermined difference from signatures of the base group.

2. The apparatus of claim 1 wherein the signatures of the base group are a subset of all other signatures in the family.

3. The apparatus of claim 1 wherein the predetermined difference is a predetermined number of extra scans in the given signatures compared to scans of the signatures of the base group.

4. The apparatus of claim 3 wherein the predetermined difference is a predetermined number of extra scans in the given signatures having a tomography machine setting of localizer mode compared to the scans of the signatures of the base group having a tomography setting of localizer mode.

5. The apparatus of claim 1 wherein the predetermined difference is a predetermined value of overlap number in the given signatures.

6. The apparatus of claim 1 wherein the electronic computer further evaluates the groups of each family and promotes at least one group outside of the base group to a new family based on the number of signatures in the group.

7. The apparatus of claim 6 wherein the text descriptions for each image include a image text description and a tomographic machine setting of the image and wherein the electronic computer further extracts a an image text description and tomographic machine setting of images of each study and wherein at least one group is promoted if at least one combination of tomographic machine setting and image text description associated with the group is unique with respect to those combinations associated with the base group and the group has the most signatures in the family except the base group.

8. The apparatus of claim 6 wherein the at least one group is promoted only if a number of signatures in the group is greater than a predetermined percentage of the number of signatures in the base group.

9. The apparatus of claim 8 wherein the predetermined percentage is greater than fifty percent.

10. The apparatus of claim 6 wherein the new family also includes groups whose signatures are supersets of the at least one promoted group.

11. The apparatus of claim 1 wherein the overlap number is a number of images of the study having at least a predetermined percentage of overlap in anatomical spans.

12. The apparatus of claim 11 wherein the predetermined percentage of overlap is greater than fifty percent.

13. The apparatus of claim 1 wherein the anatomical span is determined by at least one of a comparison of scan start and end points of the output data associated with each image and a similarity analysis of each image with respect to other images.

14. The apparatus of claim 1 wherein the generation of a signature further identifies tack-on images anatomically adjacent to an anatomical span of another image of the scan and having a length less than a predetermined percentage of the other image and wherein the predetermined difference is a number of tack-on images in the given signatures compared to the signatures of the base group.

15. The apparatus of claim 1 further including a white list having a set of words indicating studies that provide overlap and wherein the electronic computer further extracts at least one of an image text description of images of each study and at least one of a study text description of the images and compares it to the white list to output data identifying given signatures only if the at least one of the image text description and study text description of the images associated with the given signatures does not match words of the white list.

16. The apparatus of claim 14 wherein in the white list includes words indicating multiple imaging phases associated with contrast medium.

17. The apparatus of claim 1 wherein the output data excludes signatures associated with a family having only a single group.

18. The apparatus of claim 1 wherein an output data identifies given signatures as a function of at least one of the group consisting of the technician obtaining a scan of the given signatures, the protocol of the scan of the given signatures, and the tomographic machine acquiring tomographic scans of the given signatures.

19. The apparatus of claim 1 wherein the tomographic scans are scans acquired by tomographic modalities selected from the group consisting of CT, MRI, SPECT, and PET machines.

20. The apparatus of claim 1 wherein the step of extracting image signature data reviews at least one of digital imaging and communications in medicine DICOM headers of all images output from the set of machines and selected DICOM headers of selected images and a log file providing data for non-selected images.

* * * * *